(12) United States Patent
Schneider et al.

(10) Patent No.: US 11,471,212 B2
(45) Date of Patent: Oct. 18, 2022

(54) ELECTROSURGICAL DEVICES WITH MONOPOLAR AND BIPOLAR FUNCTIONALITY

(71) Applicant: Ethicon LLC, Guaynabo, PR (US)

(72) Inventors: Matthew Schneider, Blue Ash, OH (US); Mark Glassett, Madisonville, LA (US); Richard W. Timm, Cincinnati, OH (US); Chad Frampton, American Fork, UT (US); Gaetana Michelet, Bayamon, PR (US); John Brady, Cincinnati, OH (US); Michael Ehninger, South Jordan, UT (US); Gregory Bakos, Mason, OH (US); Tylor Muhlenkamp, Cincinnati, OH (US); Brian D. Bertke, Fort Thomas, KY (US); Brian Walter, South Jordan, UT (US)

(73) Assignee: Cilag GmbH International, Zug (CH)

( * ) Notice: Subject to any disclaimer, the term of this patent is extended or adjusted under 35 U.S.C. 154(b) by 540 days.

(21) Appl. No.: 16/375,375

(22) Filed: Apr. 4, 2019

(65) Prior Publication Data
US 2020/0315689 A1 Oct. 8, 2020

(51) Int. Cl.
*A61B 18/14* (2006.01)
*A61B 18/12* (2006.01)
*A61B 18/00* (2006.01)

(52) U.S. Cl.
CPC ...... *A61B 18/1445* (2013.01); *A61B 18/1206* (2013.01); *A61B 2018/0063* (2013.01);
(Continued)

(58) Field of Classification Search
CPC ............ A61B 18/1445; A61B 18/1206; A61B 2018/00589; A61B 2018/00595;
(Continued)

(56) References Cited

U.S. PATENT DOCUMENTS 5,403,312 A * 4/1995 Yates ............... A61B 17/07207
606/50
5,456,684 A * 10/1995 Schmidt ................. A61B 17/29
606/41

(Continued)

FOREIGN PATENT DOCUMENTS

EP 2926754 A2 * 10/2015 ......... A61B 18/1445

OTHER PUBLICATIONS

"Ligasure™ Retractable L-Hook Laparoscopic Sealer/Divider" brochure, Medtronic, 2016 (14 pages).
(Continued)

*Primary Examiner* — Michael F Peffley
(74) *Attorney, Agent, or Firm* — Mintz Levin Cohn Ferris Glovsky and Popeo, P.C.

(57) ABSTRACT

In general, systems, methods, and devices for electrosurgical devices with monopolar and bipolar functionality are provided. In an exemplary embodiment, a surgical device can have bipolar functionality, in which tissue engaged by the device is treated in a bipolar energy delivery mode, and can have monopolar functionality in which tissue engaged by the device is treated in a monopolar energy delivery mode.

17 Claims, 5 Drawing Sheets

(52) U.S. Cl.
CPC ............. *A61B 2018/00589* (2013.01); *A61B 2018/00595* (2013.01); *A61B 2018/00601* (2013.01); *A61B 2018/126* (2013.01); *A61B 2018/1253* (2013.01)

(58) Field of Classification Search
CPC .. A61B 2018/00901; A61B 2018/0063; A61B 2018/1253; A61B 2018/126; A61B 2018/00767; A61B 2018/00136; A61B 2018/00202; A61B 2018/00577; A61B 2018/00607; A61B 2018/00601
See application file for complete search history.

(56) References Cited

U.S. PATENT DOCUMENTS

| | | | |
|---|---|---|---|
| 6,068,627 A | 5/2000 | Orszulak et al. | |
| 6,277,117 B1 | 8/2001 | Tetzlaff et al. | |
| 6,398,779 B1 | 6/2002 | Buysse et al. | |
| 6,511,480 B1 | 1/2003 | Tetzlaff et al. | |
| 6,743,229 B2 | 6/2004 | Buysse et al. | |
| 6,796,981 B2 | 9/2004 | Wham et al. | |
| D496,997 S | 10/2004 | Dycus et al. | |
| D499,181 S | 11/2004 | Dycus et al. | |
| 6,960,210 B2 | 11/2005 | Lands et al. | |
| 7,044,949 B2 | 5/2006 | Orszulak et al. | |
| D525,361 S | 7/2006 | Hushka | |
| 7,101,371 B2 | 9/2006 | Dycus et al. | |
| 7,101,372 B2 | 9/2006 | Dycus et al. | |
| 7,101,373 B2 | 9/2006 | Dycus et al. | |
| 7,112,201 B2 | 9/2006 | Truckai et al. | |
| D531,311 S | 10/2006 | Guerra et al. | |
| 7,118,587 B2 | 10/2006 | Dycus et al. | |
| 7,147,637 B2 * | 12/2006 | Goble | A61B 18/1442 606/50 |
| 7,150,097 B2 | 12/2006 | Sremcich et al. | |
| 7,150,749 B2 | 12/2006 | Dycus et al. | |
| D535,027 S | 1/2007 | James et al. | |
| 7,156,846 B2 | 1/2007 | Dycus et al. | |
| 7,169,145 B2 | 1/2007 | Isaacson et al. | |
| 7,232,440 B2 * | 6/2007 | Dumbauld | A61B 18/1445 606/51 |
| 7,255,697 B2 | 8/2007 | Dycus et al. | |
| 7,267,677 B2 | 9/2007 | Johnson et al. | |
| 7,303,557 B2 | 12/2007 | Wham et al. | |
| 7,329,256 B2 | 2/2008 | Johnson et al. | |
| 7,364,577 B2 | 4/2008 | Wham et al. | |
| 7,377,920 B2 | 5/2008 | Buysse et al. | |
| 7,384,420 B2 | 6/2008 | Dycus et al. | |
| D575,395 S | 8/2008 | Hushka | |
| D575,401 S | 8/2008 | Hixson et al. | |
| 7,416,101 B2 | 8/2008 | Shelton, IV et al. | |
| 7,416,437 B2 | 8/2008 | Sartor et al. | |
| 7,445,621 B2 | 11/2008 | Dumbauld et al. | |
| 7,473,253 B2 | 1/2009 | Dycus et al. | |
| 7,510,556 B2 | 3/2009 | Nguyen et al. | |
| 7,553,312 B2 | 6/2009 | Tetzlaff et al. | |
| 7,582,087 B2 | 9/2009 | Tetzlaff et al. | |
| 7,597,693 B2 | 10/2009 | Garrison | |
| 7,641,653 B2 | 1/2010 | Dalla Betta et al. | |
| 7,722,607 B2 | 5/2010 | Dumbauld et al. | |
| D617,900 S | 6/2010 | Kingsley et al. | |
| D618,798 S | 6/2010 | Olson et al. | |
| 7,766,910 B2 | 8/2010 | Hixson et al. | |
| 7,789,878 B2 | 9/2010 | Dumbauld et al. | |
| D627,462 S | 11/2010 | Kingsley | |
| 7,846,161 B2 | 12/2010 | Dumbauld et al. | |
| 7,947,041 B2 | 5/2011 | Tetzlaff et al. | |
| D649,249 S | 11/2011 | Guerra | |
| 8,070,748 B2 | 12/2011 | Hixson et al. | |
| 8,105,323 B2 | 1/2012 | Buysse et al. | |
| 8,241,284 B2 | 8/2012 | Dycus et al. | |
| 8,287,528 B2 | 10/2012 | Wham et al. | |
| D670,808 S | 11/2012 | Moua et al. | |
| 8,323,310 B2 | 12/2012 | Kingsley | |
| 8,361,072 B2 | 1/2013 | Dumbauld et al. | |
| 8,647,341 B2 | 2/2014 | Dycus et al. | |
| 8,668,689 B2 | 3/2014 | Dumbauld et al. | |
| RE44,834 E | 4/2014 | Dumbauld et al. | |
| 8,968,311 B2 | 3/2015 | Allen, IV et al. | |
| D726,910 S | 4/2015 | Lacosta et al. | |
| 9,005,200 B2 | 4/2015 | Roy et al. | |
| 9,017,372 B2 | 4/2015 | Artale et al. | |
| 9,039,691 B2 | 5/2015 | Moua et al. | |
| 9,072,524 B2 | 7/2015 | Heard et al. | |
| D736,920 S | 8/2015 | Lee et al. | |
| D744,100 S | 11/2015 | Chang et al. | |
| D744,644 S | 12/2015 | Lee et al. | |
| D748,260 S | 1/2016 | Chang et al. | |
| 9,232,974 B2 | 1/2016 | Dycus et al. | |
| 9,241,759 B2 | 1/2016 | Dycus et al. | |
| D750,245 S | 2/2016 | Chang et al. | |
| 9,358,028 B2 | 6/2016 | Moua et al. | |
| 9,375,263 B2 | 6/2016 | Allen, IV et al. | |
| 9,375,270 B2 | 6/2016 | Wham et al. | |
| 9,375,271 B2 | 6/2016 | Wham et al. | |
| 9,381,060 B2 | 7/2016 | Artale et al. | |
| 9,456,863 B2 | 10/2016 | Moua | |
| 9,468,491 B2 | 10/2016 | Brandt et al. | |
| 9,492,221 B2 * | 11/2016 | Garrison | A61B 18/1442 |
| 9,492,225 B2 | 11/2016 | Dycus et al. | |
| 9,498,279 B2 | 11/2016 | Artale et al. | |
| D774,190 S | 12/2016 | Lee et al. | |
| 9,539,054 B2 | 1/2017 | Peterson et al. | |
| 9,549,775 B2 | 1/2017 | Dumbauld et al. | |
| 9,592,089 B2 | 3/2017 | Lyons et al. | |
| D788,302 S | 5/2017 | O'Neill et al. | |
| 9,649,152 B2 | 5/2017 | Moua et al. | |
| 9,655,672 B2 | 5/2017 | Artale et al. | |
| 9,655,673 B2 | 5/2017 | McCullough, Jr. et al. | |
| 9,675,405 B2 | 6/2017 | Trees et al. | |
| 9,713,492 B2 | 7/2017 | Garrison et al. | |
| 9,717,548 B2 * | 8/2017 | Couture | A61B 18/1445 |
| 10,010,309 B2 | 7/2018 | Bingham | |
| 10,010,366 B2 | 7/2018 | Strobl | |
| 2007/0106297 A1 * | 5/2007 | Dumbauld | A61B 18/085 606/51 |
| 2014/0276794 A1 * | 9/2014 | Batchelor | A61B 18/1445 606/42 |
| 2015/0313628 A1 * | 11/2015 | Allen, IV | A61B 17/320092 606/171 |
| 2017/0135712 A1 | 5/2017 | Boudreaux | |
| 2017/0238991 A1 | 8/2017 | Worrell et al. | |

OTHER PUBLICATIONS

U.S. Appl. No. 16/375,338 entitled "Surgical Devices Switchable Between Monopolar Functionality and Bipolar Functionality" filed Apr. 4, 2019 (43 pages).

International Search Report and Written Opinion received for PCT Application No. PCT/IB2020/052710 dated Jun. 26, 2020 (14 pages).

* cited by examiner

ELECTROSURGICAL DEVICES WITH MONOPOLAR AND BIPOLAR FUNCTIONALITY

FIELD

The present disclosure relates generally to electrosurgical devices with monopolar and bipolar functionality.

BACKGROUND

Various surgical devices can be used for minimally-invasive surgery to compress, transect, and seal different types of tissue. In general, these devices can have an end effector with a pair of opposed jaws that are configured to engage tissue therebetween, and can have a cutting mechanism that is configured to transect tissue engaged by the opposed jaws. The end effector can be configured to apply electrical energy to tissue engaged between the opposed jaws. The application of electrical energy to the engaged tissue can seal and coagulate the tissue, such as to seal tissue being cut by the cutting mechanism to prevent or reduce bleeding.

However, various situations can arise during an operation in which a user wants to apply energy to tissue without having to first grasp tissue between the opposed jaws, such as to selectively apply energy to spots of tissue in a controlled manner without having to clamp and seal an entire section of tissue.

Accordingly, there remains a need for improved energy delivery from surgical devices to tissue.

SUMMARY

In general, systems, methods, and devices for electrosurgical devices with monopolar and bipolar functionality are provided.

In one aspect, an electrosurgical device is provided that in one embodiment includes a housing, an elongate shaft extending from the housing, and an end effector coupled to a distal end of the elongate shaft. The end effector includes first and second jaws. At least one of the first and second jaws are pivotable relative to the other to move the end effector between an open position and a closed position. The device also includes first and second electrode portions on the first jaw. The first electrode portion is in surrounding relation along a perimeter of the second electrode portion such that the first electrode portion is positioned laterally outward of the second electrode portion. The first electrode portion is configured to be exposed along an edge of the first jaw with the end effector in the closed position and with the end effector in the open position. In a bipolar mode of operation the second electrode portion is configured to deliver energy to tissue engaged by the end effector, and the first electrode portion is disabled from delivering energy to tissue engaged by the end effector. In a monopolar mode of operation the first electrode portion is configured to deliver energy to tissue.

The device can have any number of variations. For example, in the monopolar mode of operation the second electrode portion is one of disabled from delivering energy to tissue and enabled to deliver energy to tissue. For another example, the second jaw can have a width that is less than a combined width of the first and second electrode portions. For yet another example, a single electrode can include the first and second electrode portions with the first electrode portion in surrounding relation along the perimeter of the second electrode portion, which is in direct contact with the first electrode portion. For still another example, the device can include a return electrode on the second jaw, and the return electrode can be configured for energy return in the bipolar mode of operation. For another example, the first electrode portion can be in surrounding relation along the perimeter of the second electrode portion only along a distal tip of the first jaw and along a single lateral edge of the first jaw. For yet another example, the first electrode portion can be in surrounding relation along the perimeter of the second electrode portion only along a single lateral edge of the first jaw.

For another example, the device can also include a sensor configured to sense when the end effector is in the closed position, and an actuator configured to be actuated to cause energy delivery in the bipolar mode of operation only with the end effector in the closed position as sensed by the sensor. In at least some embodiments, the monopolar mode of operation can only be possible with the end effector in the open position. In at least some embodiments, the device can include a second actuator configured to be actuated to cause energy delivery in the monopolar mode of operation.

For yet another example, a first electrode can include the first electrode portion, a second, different electrode can include the second electrode portion, and the device can further include an insulator in surrounding relation along the perimeter of the second electrode so as to be sandwiched between the first and second electrodes.

In still another example, the first electrode portion can be in surrounding relation along the perimeter of the second electrode portion along a distal tip of the first jaw and along two lateral edges of the first jaw. In at least some embodiments, the monopolar mode of operation can be possible with the end effector in the open position and in the closed position.

In another example, a single electrode can include the first and second electrode portions, and the first electrode portion, but not the second electrode portion, can have a coating thereon.

In another embodiment, an electrosurgical device includes a housing, an elongate shaft extending from the housing, and an end effector coupled to a distal end of the elongate shaft. The end effector includes first and second jaws. At least one of the first and second jaws is pivotable relative to the other to move the end effector between an open position and a closed position. An electrode on the first jaw extends laterally outward from an outer edge of the first jaw such that with the end effector in the closed position the electrode is exposed, thereby allowing the electrode to contact tissue with the end effector in the closed position and without any tissue being engaged between the first and second jaws. The electrode is configured to deliver energy to tissue with the end effector in the open position and with the end effector in the closed position.

The device can have any number of variations. For example, the electrode can be a single electrode, a first portion of the electrode can extend laterally outward from the outer edge of the first jaw and can be in surrounding relation along a perimeter of a second portion of the electrode such that the first portion of the electrode is positioned laterally outward of the second portion of the electrode, in a bipolar mode of operation the second portion of the electrode can be configured to deliver energy to tissue and the first portion of the electrode is disabled from delivering energy to tissue, and in a monopolar mode of operation the first portion of the electrode can be configured to deliver energy to tissue.

For another example, the device can include a second, different electrode on the first jaw, the electrode can be in surrounding relation along a perimeter of the second electrode such that the electrode is positioned laterally outward of the second electrode, in a bipolar mode of operation the second electrode can be configured to deliver energy to tissue and the electrode can be disabled from delivering energy to tissue, in a monopolar mode of operation the first electrode can be configured to deliver energy to tissue and the second electrode can be disabled from delivering energy to tissue, the device can further include a return electrode on the second jaw, and the return electrode can be configured for energy return in the bipolar mode of operation. In at least some embodiments, the device can further include a sensor configured to sense when the end effector is in the closed position, and an actuator configured to be actuated to cause energy delivery in the bipolar mode of operation only with the end effector in the closed position as sensed by the sensor. In at least some embodiments, the monopolar mode of operation can be possible with the end effector in the open position and in the closed position.

In another aspect, a surgical method is provided that in one embodiment includes positioning an end effector of a surgical device in contact with tissue. The end effector is coupled to a distal end of an elongate shaft of the surgical device, the end effector includes first and second jaws, and first and second electrode portions are on the first jaw with the first electrode portion being in surrounding relation along a perimeter of the second electrode portion such that the first electrode portion is positioned laterally outward of the second electrode portion. The method also includes activating the surgical device in a bipolar mode of operation such that the second electrode portion, but not the first electrode portion, delivers energy to the tissue. The method also includes activating the surgical device in a monopolar mode of operation such that the first electrode portion delivers energy to the tissue.

The method can vary in any number of ways. For example, in the monopolar mode of operation the second electrode portion can not deliver energy to the tissue. For another example, the method can further include sensing with a sensor when the end effector is in a closed position, activating the surgical device in the bipolar mode of operation can only be possible with the end effector in the closed position as sensed by the sensor, and activating the surgical device in the monopolar mode of operation can only be possible with the end effector in an open position. For yet another example, activating the surgical device in the monopolar mode of operation can be possible with the end effector in an open position and in a closed position.

BRIEF DESCRIPTION OF DRAWINGS

This invention will be more fully understood from the following detailed description taken in conjunction with the accompanying drawings, in which.

DETAILED DESCRIPTION

Figure 1:
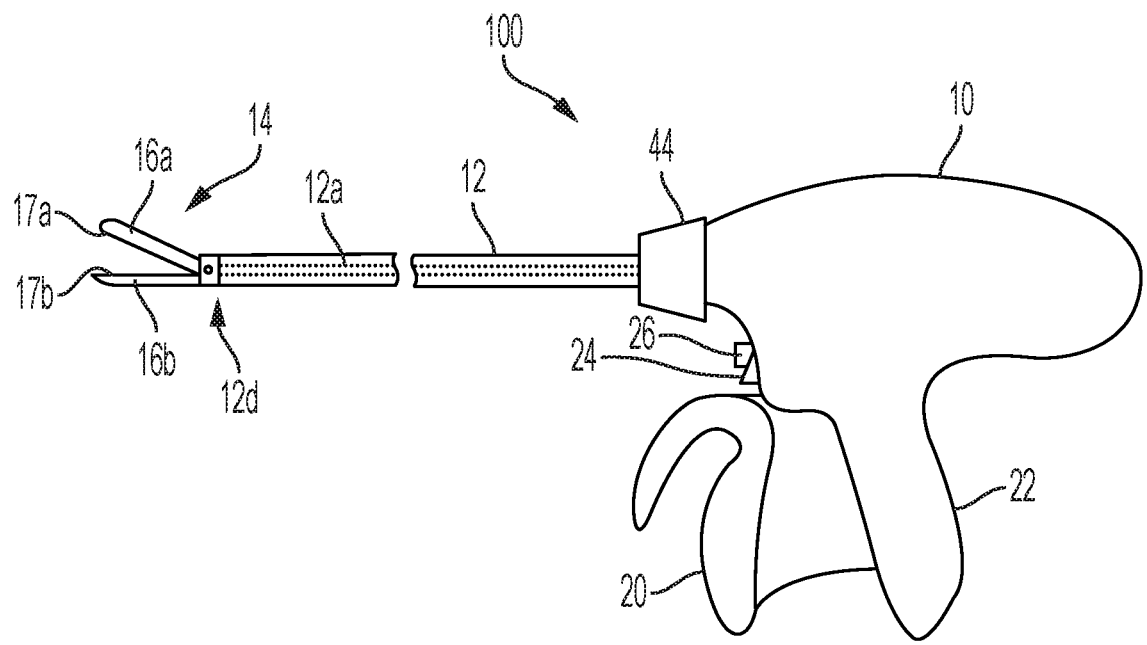
FIG. 1 is a side schematic view of one embodiment of a surgical device.

Certain exemplary embodiments will now be described to provide an overall understanding of the principles of the structure, function, manufacture, and use of the devices, systems, and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. A person skilled in the art will appreciate that a dimension may not be a precise value but nevertheless be considered to be at about that value due to any number of factors such as manufacturing tolerances and sensitivity of measurement equipment. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

In general, systems, methods, and devices for electrosurgical devices with monopolar and bipolar functionality are provided. In an exemplary embodiment, a surgical device can have bipolar functionality, in which tissue engaged by the device is treated in a bipolar energy delivery mode, and can have monopolar functionality in which the tissue engaged by the device is treated in a monopolar energy delivery mode. The device can include a single electrode including a first portion configured to deliver energy in the device's bipolar energy delivery mode and a second portion configured to deliver energy in the device's monopolar energy delivery mode and in at least partial surrounding relation to the first portion of the electrode. In other embodiments, a first electrode is configured to deliver energy in the device's bipolar delivery mode and a second electrode is configured to deliver energy in the device's monopolar delivery mode and in at least partial surrounding relation to the first electrode.

FIG. 1 illustrates one embodiment of a surgical device configured to grasp and cut tissue. The illustrated surgical device 100 includes a housing 10, an elongate shaft 12, and an end effector 14 configured to grasp tissue. The housing 10 can be any type of pistol-grip, scissor grip, pencil-grip, or other type of handle known in the art that is configured to carry various actuators, such as actuator levers, knobs, triggers, sliders, etc. for actuating various functions such as rotating, articulating, approximating, and/or firing the end effector 14. In the illustrated embodiment, the housing 10 is coupled to a stationary grip handle 22 and a closure grip handle 20 configured to move relative to the stationary grip handle 22 to open and close the end effector 14. The shaft 12 extends distally from the housing 10 and includes at least one lumen 12a extending therethrough for carrying mechanisms for actuating the end effector 14.

The end effector 14 can have a variety of sizes, shapes, and configurations. As shown in FIG. 1, the end effector 14 includes a first, lower jaw 16b and a second, upper jaw 16a disposed at a distal end 12d of the shaft 12. The jaws 16a, 16b are configured to move between an open position, in which the jaws 16a, 16b are spaced a distance apart, and a clamping or closed position, in which the jaws 16a, 16b are moved toward one another and are substantially opposed. The jaws 16a, 16b in the closed position are to engage tissue therebetween and apply a force to tissue disposed therebetween. In the illustrated embodiment, the end effector 14 is configured to move between the open and closed positions by the upper jaw 16a pivoting relative to the shaft 12 and relative to the lower jaw 16b while the lower jaw 16b remains stationary. In other embodiments, both jaws 16a, 16b can be movable to move the end effector 14 between the open and closed positions, or the lower jaw 16b can be configured to pivot relative to the shaft 12 and the upper jaw 16a to move the end effector 14 between the open and closed positions.

While the illustrated jaws 16a, 16b are each curved to one side along a longitudinal length thereof, a person skilled in the art will appreciate that one or both of the jaws 16a, 16b can have other shapes, such as being curved in an opposite direction or having a substantially elongate and straight shape. The jaws 16a, 16b can have any suitable axial length for engaging tissue, and the length can be selected based on the targeted anatomical structure for transection and/or sealing.

The device 100 includes a knob 44 operatively coupled to the shaft 12 and the end effector 14. The knob 44 is configured to be rotated relative to the housing 10 to cause the shaft 12 and the end effector 14 to rotate about a longitudinal axis of the shaft 12.

The closure handle 20 is configured to pivot relative to and toward and away from stationary handle 22 to move the end effector 14 between the open and closed positions. In particular, the closure handle 20 is movable between a first position and a second position. In the first position, which is illustrated in FIG. 1, the closure handle 20 is offset and spaced apart from the stationary handle 22, and the jaws 16a, 16b of the end effector 14 are open. In at least some embodiments the closure handle 20 is biased to the first position such that the end effector 14 is biased to be open. In the second position the closure handle 20 is positioned adjacent to, or substantially in contact with, the stationary handle 22, and the jaws 16a, 16b of the end effector 14 are closed. Further description of embodiments of end effector opening and closing is provided in U.S. Pat. No. 10,010,309 entitled "Surgical Device With Overload Mechanism" filed Oct. 10, 2014, which is hereby incorporated by reference in its entirety.

In at least some embodiments the device 100 includes a locking feature configured to lock the closure handle 20 in position relative to the stationary handle 22, as will be appreciated by a person skilled in the art. For example, the locking feature can be configured to automatically engage when the closure handle 20 is moved to the second position, e.g., is positioned adjacent to, or substantially in contact with, the stationary handle 22. For another example, the locking feature can be configured to automatically engage at each of a plurality of positions the closure handle 20 is pivoted through between the first and second positions, such as via ratcheting.

The closure handle 20 can use manual or powered components. In manual embodiments the closure handle 20 is configured to be manually moved (e.g., by a user directly or by a user indirectly via robotic surgical control) to manually open/close the end effector 14 using various components, e.g., gear(s), rack(s), drive screw(s), drive nut(s), etc. disposed within the housing 10 and/or shaft 12.

Figure 2:
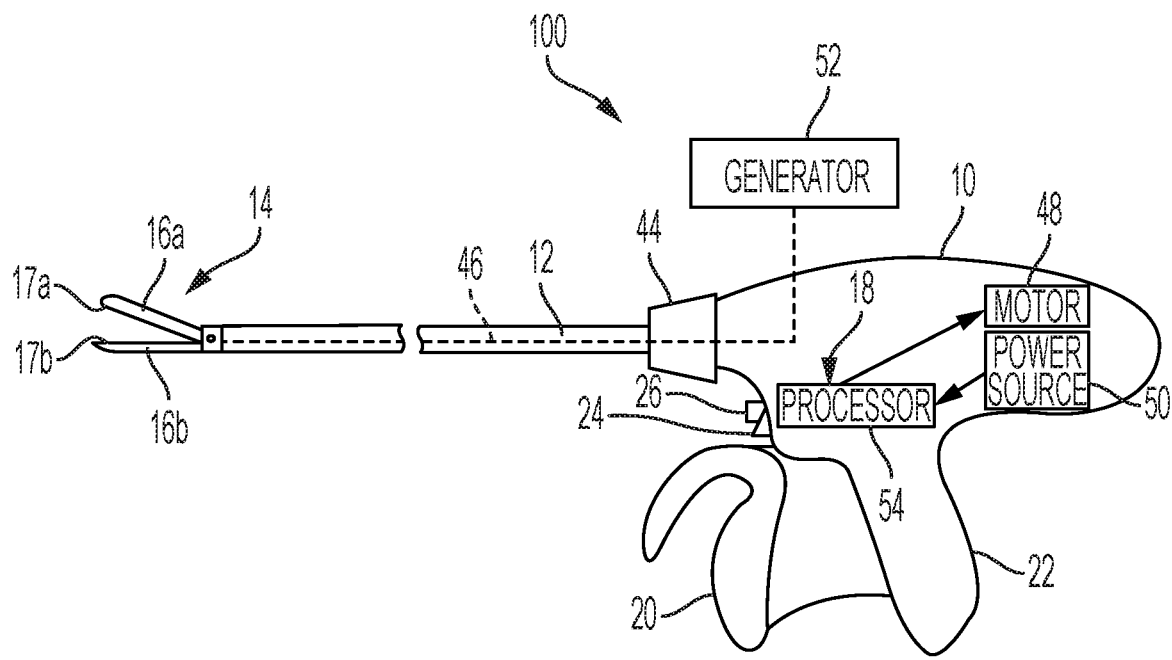
FIG. 2 is a side, partially transparent view of the surgical device of FIG. 1 operatively coupled to a generator.

In powered embodiments, the closure handle 20 is configured to be manually moved (e.g., by a user directly or by a user indirectly via robotic surgical control), thereby causing the end effector 14 to open/close either fully electronically or electronically in addition to manual power. In this illustrated embodiment, as shown in FIG. 2, the device 100 is powered and includes a motor 48, a power source 52, and a processor 54, which in this illustrated embodiment are each disposed in the housing 10. Manual movement of the closure handle 20 is configured to cause the processor 54 to transmit a control signal to be sent to the motor 48, which is configured to interact with various components of the device 100 to cause the jaws 16a, 16b to open/close. The power source 52 is configured to provide on-board power to the processor 54 and the motor 48. In other embodiments, the processor 54 and/or the motor 48 can be configured to be powered instead, or additionally, with an external power source. The device 100 can include one or more sensors 18 to facilitate powered end effector opening and closing and/or other device features, such as tissue cutting. Various embodiments of such sensors are further described in U.S. Pat. No. 7,416,101 entitled "Motor-Driven Surgical Cutting And Fastening Instrument With Loading Force Feedback" filed Jan. 31, 2006 and U.S. Pat. No. 9,675,405 entitled "Methods And Devices For Controlling Motorized Surgical Devices" filed Apr. 8, 2014, which are hereby incorporated by reference in their entireties.

Figure 3:
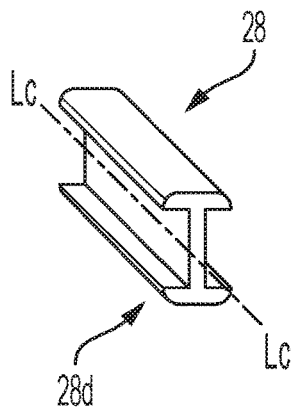
FIG. 3 is a perspective view of a compression member of the surgical device of FIG. 1.
Figure 4:
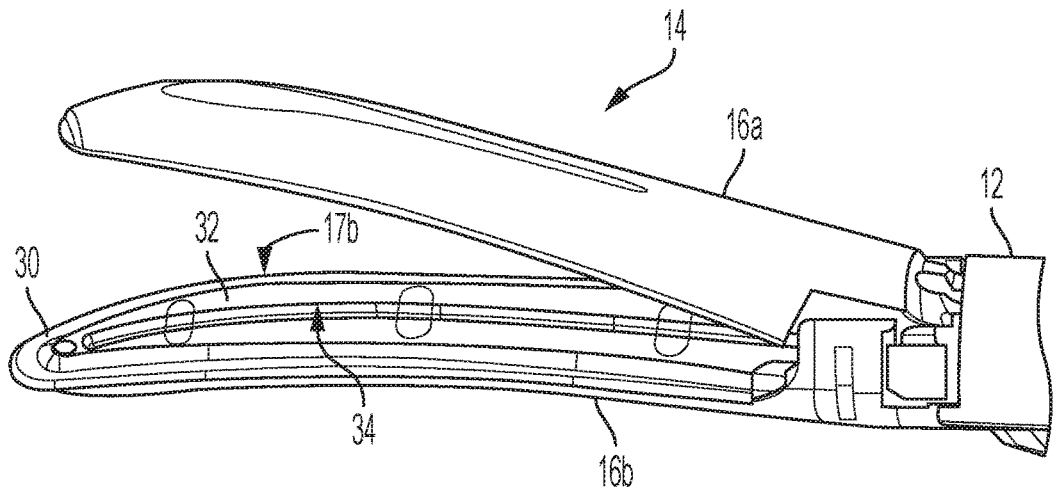
FIG. 4 is a perspective view of a distal portion of the device of FIG. 1 with the device's jaws open.

The surgical device 100 includes a cutting or firing actuator 24 configured to be actuated to advance a cutting element to cut tissue grasped between the jaws 16a, 16b. While the actuator 24 can have various configurations, e.g., buttons, knobs, triggers, etc., the illustrated actuator 24 is a button configured to be depressed. The cutting actuator 24 can be in mechanical or electrical communication with various gear(s), rack(s), drive screw(s), drive nut(s), motor(s) (e.g., the motor 48), and/or processor(s) (e.g., the processor 54) to cause the cutting element's movement when the cutting actuator 24 is actuated. The cutting element is configured to transect tissue captured between the jaws 16a, 16b and can be sized and shaped to transect or cut various thicknesses and types of tissue. In one exemplary embodiment, as shown in FIG. 3, an I-beam compression member 28 is configured to travel along a longitudinal axis Lc through slots formed in each jaw 16a, 16b to pull the jaws into a parallel orientation, to compress tissue therebetween, and to transect tissue using a cutting element on the distal end 28d thereof, such as by the distal end 28d having a sharp cutting edge or having a knife blade mounted thereon.

The surgical device 100 includes a sealing actuator 26 configured to be actuated to cause energy, such as radiofrequency (RF) or ultrasound energy, to be applied to tissue engaged by the end effector 14. While the actuator 26 can have various configurations, e.g., buttons, knobs, triggers, etc., the illustrated actuator 26 is a button configured to be depressed. In other embodiments, instead of including a cutting actuator 24 and a sealing actuator 26, a surgical device can include a combined cutting and sealing actuator configured to be actuated to simultaneously cause cutting and sealing.

The device 100 includes various components configured to facilitate the delivery of energy to tissue. These components can be disposed at various locations in the device 100, such as in the proximal handle portion 10 and/or in one or both of the jaws 16a, 16b. Actuating the sealing actuator 26 is configured to cause a signal to be transmitted to the processor 54, which in response is configured to cause delivery of energy from a generator 52 and/or the power source 50 to tissue engaged by the end effector 14. The generator 52 can be incorporated into the handle portion 10 or, as in this illustrated embodiment as shown in FIG. 2, can be a separate unit that is electrically connected to the surgical device 100. The generator 52 is any suitable generator known in the art, such as an RF generator or an ultrasound generator.

The lumen 12a of the shaft 12 has disposed therein one or more electrical paths 46, e.g., leads, conductive members, wires, etc., configured to deliver electrical energy to the end effector 14 in response to actuation of the sealing actuator 26. The one or more electrical paths 46 are operatively coupled to the generator 52 in this illustrated embodiment, with the generator 52 being configured to supply energy to the one or more electrical paths 46. Upon actuation of energy delivery, energy is configured to be delivered to one or more electrodes in one or both of the jaws 16a, 16b via the one or more electrical paths 46 for delivering electrical current to tissue grasped therebetween to effect sealing, marking, cutting, etc. of the tissue. Further description of embodiments of energy application by surgical devices is provided in U.S. Pat. No. 10,010,366 entitled "Surgical Devices And Methods For Tissue Cutting And Sealing" filed Dec. 17, 2014, U.S. Pat. No. 7,169,145 entitled "Tuned Return Electrode With Matching Inductor" filed Nov. 21, 2003, U.S. Pat. No. 7,112,201 entitled "Electrosurgical Instrument And Method Of Use" filed Jan. 22, 2003, and U.S. Patent Pub. No. 2017/0135712 entitled "Methods And Devices For Auto Return Of Articulated End Effectors" filed Nov. 17, 2015, which are hereby incorporated by reference in their entireties.

A surgeon or other medical professional may want to apply each of bipolar energy and monopolar energy during the course of performing a surgical procedure. Bipolar energy can be useful for focused energy application to tissue since the energy is applied to the grasped tissue. Monopolar energy is not as focused since the tissue may serve as the return pole and since the energy is not being applied to tissue located between and being pressed by the end effector's jaws 16a, 16b. Monopolar energy is still useful, however, such as for cutting tissue that the surgeon or other medical professional not does want to bleed, as monopolar energy is configured to be hot enough to provide for coagulation.

The device 100 has a bipolar mode of operation (also referred to herein as a "bipolar delivery mode") in which energy applied to tissue engaged by the end effector 14 is energy applied by a delivery or active electrode 17b and received by a return electrode 17a. One of the jaws 16a, 16b (the lower jaw 16b in this illustrated embodiment) includes the active electrode 17b on a tissue-facing surface thereof, and the other one of the jaws 16a, 16b (the upper jaw 16a in this illustrated embodiment) includes the return electrode 17a on a tissue-facing surface thereof. The return electrode 17a is electrically isolated from the active electrode 17b such that energy can be applied to tissue grasped between the jaws 16a, 16b from the active electrode 17b and have a return path through the return electrode 17a. The energy is thus configured to be delivered to tissue grasped between the jaw 16a, 16b when the end effector 14 is in the closed position.

The device 100 also has a monopolar mode of operation (also referred to herein as a "monopolar delivery mode") in which energy in which energy applied to tissue engaged by the end effector 14 is energy applied by the active electrode 17b. The same electrode 17b is thus configured to apply energy in the bipolar delivery mode and to apply energy in the monopolar delivery mode, as discussed further below. An energy return path during monopolar energy application can be through surrounding tissue, through the device 100 generally, through a ground pad placed on a patient's body, etc. The return electrode 17a, or the return path therefor, is inactive or disabled during energy application in the monopolar delivery mode. While tissue sealing can be accomplished in the bipolar mode of operation by applying energy to tissue grasped by the end effector 14 (e.g., located and clamped between the jaws 16a, 16b), it can be beneficial to apply spot energy to target tissue that is adjacent to the end effector 14 and not grasped thereby (e.g., located outside of the jaws 16a, 16b) to allow for spot coagulation, non-clamping sealing and/or hemostasis, marking tissue, cutting or searing tissue, etc. The device's monopolar mode of operation allows for this spot energy application.

FIGS. 4-7 illustrate the active electrode 17b in further detail. The active electrode 17b includes a first portion 30 and a second portion 32. The second electrode portion 32 is in direct contact with the first electrode portion 30 since the first and second portions 30, 32 are part of the same electrode 17b. The first portion 30 is defined by a portion of the electrode 17b that has a coating thereon, e.g., the electrode 17b has a coating thereon in the first portion 30 and lacks a coating thereon in the second portion 32. The coating allows energy to pass therethrough, but the energy deliverable through the coating, e.g., through the first electrode portion 30 in which the coating is located, requires more power than energy that is deliverable through the electrode 17b without coating, e.g., through the second electrode portion 32 that lacks the coating. Examples of materials that can form the coating include polytetrafluoroethylene (PTFE). The device 100 is thus configured to selectively allow and prevent energy to be delivered through the first electrode portion 30 by varying the voltage provided thereto, with higher voltage, e.g., a voltage above about 400 V or a voltage above about 500 V, allowing energy delivery therethrough and lower voltage, e.g., a voltage below about 300 V or a voltage below about 400 V, preventing energy delivery therethrough.

The second portion 32 of the electrode 17b is located on a tissue-facing surface of the first jaw 16b. A slot 34 extends longitudinally through the second electrode portion 32 and is configured for the compression member 28 (or the device's cutting element if not included on the compression member 28) to slide therein. The return electrode 17a on a tissue-facing surface of the second jaw 16a similarly has a slot (obscured in the figures) extending longitudinally therealong in which the compression member 28 (or the device's cutting element if not included on the compression member 28) is configured to slide.

The first portion 30 of the electrode 17b is in surrounding relation along a perimeter of the second portion 32 of the electrode 17b such that the first portion 30 is positioned laterally outward of the second portion 32. In this illustrated embodiment the first electrode portion 30 is U-shaped and extends continuously along substantially the entirety of the second electrode portion's longitudinal sides and around a distal tip thereof connecting the second electrode portion's longitudinal sides. A person skilled in the art will appreciate that the first electrode portion 30 may not extend along the entirety of the second electrode portion's longitudinal sides but nevertheless be considered to extend substantially along the entirety of the second electrode portion's longitudinal sides due to any number of factors, such as manufacturing tolerances, sensitivity of measurement equipment, etc. The first electrode portion 30 being so shaped and located may help ensure that energy can be applied to tissue as desired by a user of the device 100 with no or minimal reorientation of the end effector 14 within a patient's body since the first electrode portion 30 extends substantially along an entire perimeter of the end effector 14. The first electrode portion 30 being located around the distal tip may facilitate targeted energy application to a relatively small area of tissue. The first electrode portion 30 being located along the longitudinal sides may facilitate energy application along a length of tissue to allow the entire length to be, e.g., cut and coagulated. In other embodiments, the first electrode portion 30 can be located only around a distal tip of the second electrode portion 32 and not along the second electrode portion's longitudinal sides, only along the second electrode portion's longitudinal sides and not around the distal tip connecting the longitudinal sides, or along only one of the second electrode portion's longitudinal sides and not around the distal tip connecting the longitudinal sides.

Figure 7:
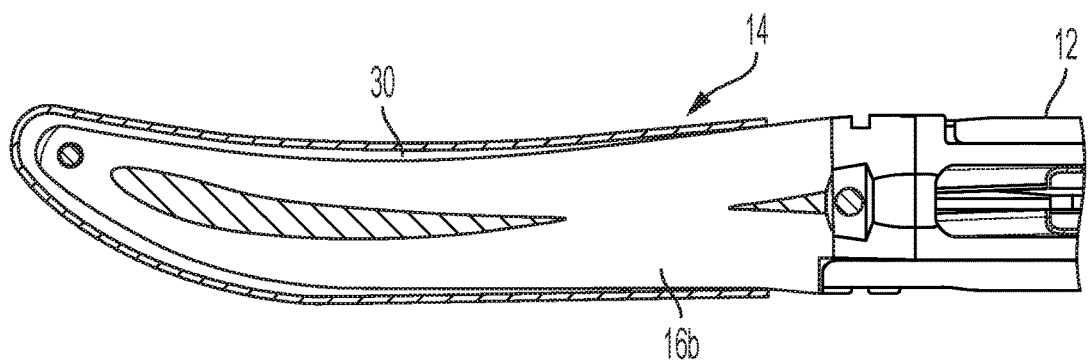
FIG. 7 is a bottom view of the distal portion of the device of FIG. 5.
Figure 8:
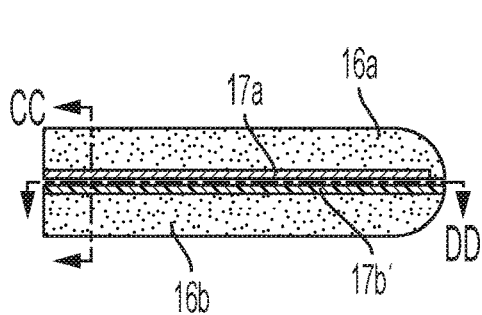
FIG. 8 is a side schematic cross-sectional view of a distal portion of another embodiment of a surgical device with the device's jaws closed.
Figure 9:
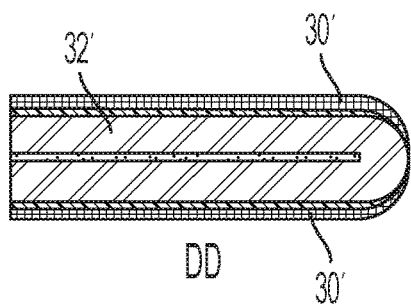
FIG. 9 is a schematic cross-sectional view of the device of FIG. 8.
Figure 10:
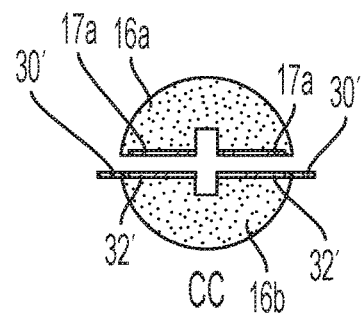
FIG. 10 is another schematic cross-sectional view of the device of FIG. 8.

FIGS. 8-10 illustrate an alternate embodiment of an active electrode 17b' in which a first electrode portion 30' of the electrode 17b' is only along the longitudinal sides of a second electrode portion 32' of the electrode 17b' and not around a distal tip connecting the longitudinal sides. The end effector 14 and device 100 including the end effector 14 are otherwise configured and used similar to that discussed above regarding FIGS. 1-7 and can include any number of the alternate features described with respect to FIGS. 1-7.

Figure 5:
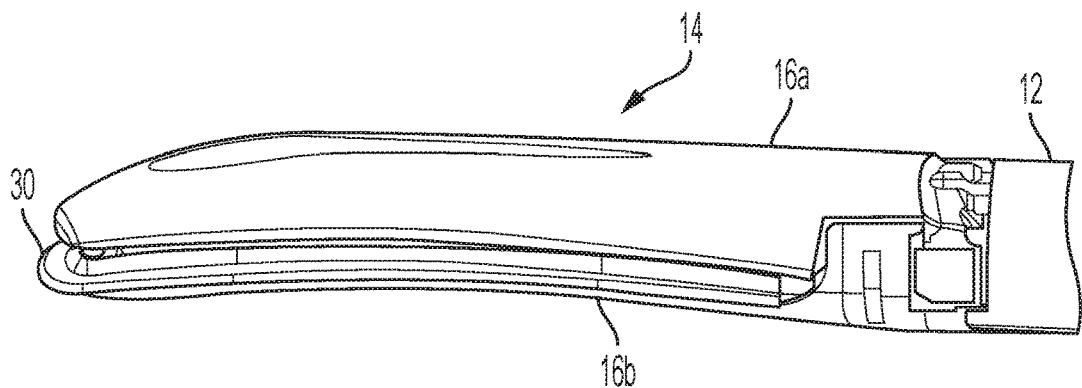
FIG. 5 is a perspective view of the distal portion of the device of FIG. 4 with the jaws closed.
Figure 6:
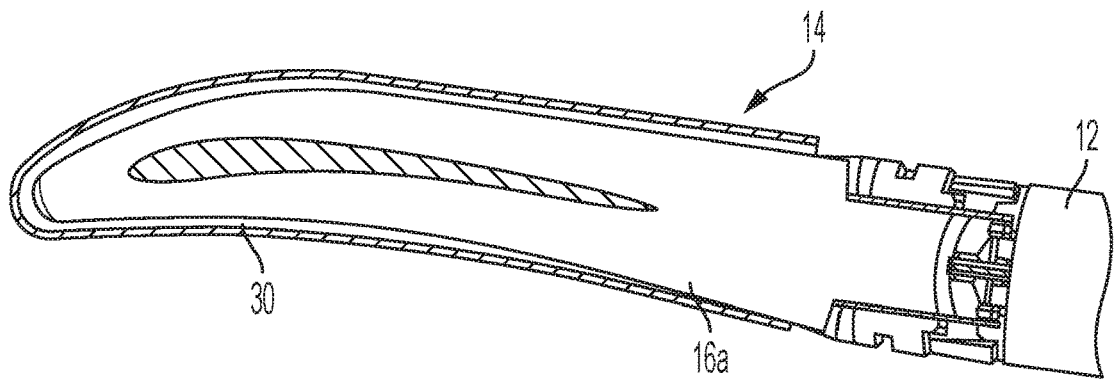
FIG. 6 is a top view of the distal portion of the device of FIG. 5.

Referring again to the embodiment of FIGS. 1-7, the first electrode portion 30 is configured to be exposed along an edge of the first jaw 16b with the jaws 16a, 16b open (FIGS. 1, 2, and 4) and with the jaws 16a, 16b closed (FIGS. 5-7). In other words, the first portion 30 of the electrode 17b overhangs the first jaw 16b. In this illustrated embodiment the first jaw 16b has a width that is less than a combined width of the first and second electrode portions 30, 32 to facilitate the first electrode portion's overhang. The amount of overhang can be, for example, in a range of about 0.010" to 0.30" on each side of the first jaw 16b. In an exemplary embodiment, a total width of the first jaw 16b including the overhang is configured to allow the first jaw 16b to fit through a trocar, such as a 5 mm trocar having an inner diameter in a range of about 0.220" to 0.230". The second jaw 16a is substantially the same size as the first jaw 16b, so the second jaw 16a does not prevent the first electrode portion 30 from being exposed when the jaws 16a, 16b are open or when the jaws 16a, 16b are closed. The second jaw 16a thus also has a width that is less than a combined width of the first and second electrode portions 30, 32 to facilitate the first electrode portion's overhang. A person skilled in the art will appreciate that the first and second jaws 16a, 16b may not be precisely the same size but nevertheless be considered to be substantially the same size due to any number of factors, such as manufacturing tolerances, sensitivity of measurement equipment, etc. The exposure of the first electrode portion 30 regardless of whether the jaws 16a, 16b are open or closed provides flexibility to a user of the device 100 since energy can be applied to tissue via the first electrode portion 30 regardless of whether the jaws 16a, 16b are open or closed.

The second electrode portion 32 is configured to be exposed with the jaws 16a, 16b open and to not be exposed with the jaws 16a, 16b closed. Similarly, the return electrode 17a is configured to be exposed with the jaws 16a, 16b open and to not be exposed with the jaws 16a, 16b closed.

The first portion 30 of the electrode 17b is configured to delivery energy in the monopolar mode of operation, and the second portion 32 of the electrode 17b is configured to deliver energy in the bipolar mode of operation. The same electrode 17b can thus be configured to deliver, at different times, both energy for monopolar functionality and for bipolar functionality.

The device 100 is configured to selectively operate in the bipolar delivery mode, in which bipolar energy is applied via the second portion 32 of the electrode 17b, and the monopolar delivery mode, in which monopolar energy is applied via the first portion 30 of the electrode 17b. The device 100 can be configured to change between the bipolar delivery mode and the monopolar delivery mode in any of a variety of ways.

In one exemplary embodiment, the sealing actuator 26 is not a single actuator as illustrated in FIGS. 1 and 2 but instead includes a first sealing actuator configured to be actuated to cause bipolar energy delivery and a second sealing actuator configured to be actuated to cause monopolar energy delivery. The one of the first and second actuators that is actuated defines whether the device 100 is in the bipolar delivery mode or the monopolar delivery mode.

In another exemplary embodiment, the device 100 includes a mode selector, e.g., a switch, a knob, a lever, etc., accessible at the housing 10 to a user. The mode selector is configured to move between a first position, indicative of bipolar delivery mode selection, and a second position, indicative of a monopolar delivery mode selection. Depending on whether the mode selector is in the first position or the second position, actuation of the sealing actuator 26 is configured to cause either energy delivery in the bipolar mode of operation (mode selector in the first position) or energy delivery in the monopolar mode of operation (mode selector in the second position). The mode selector can be configured to provide a signal to the processor 54 indicative of the mode selector's position, or the sensor 18 of the device 100 can configured to sense whether the mode selector is in the first position or second position and provide a signal to the processor 54 indicative of the mode selector's position. The processor 54 is configured to direct energy, e.g., from the generator 52, to the active one of the current path for the device's bipolar energy circuit (bipolar delivery mode) and the current path for the device's monopolar energy circuit (monopolar delivery mode). For monopolar delivery mode the processor 54 is also configured to disable or otherwise inactivate the return electrode 17a or the return electrode's return path.

Embodiments of changing between monopolar and bipolar delivery modes of a surgical device are further described in U.S. patent application Ser. No. 16/375,338 entitled "Surgical Devices Switchable Between Monopolar Functionality And Bipolar Functionality" filed on Apr. 4, 2019, which is incorporated by reference in its entirety.

In the illustrated embodiment of FIGS. 1-7 the second portion 32 of the electrode 17b is configured to deliver energy in the monopolar mode of operation in addition to the first portion 30 of the electrode 17b being configured to deliver energy in the monopolar mode of operation because the first and second electrode portions 30, 32 are not electrically isolated from one another. In other words, the entire electrode 17b is configured to deliver energy in the monopolar delivery mode, and the second electrode portion 32 but not the first electrode portion 30 is configured to deliver energy in the bipolar mode of operation. Because energy can be desirable to apply to tissue in the monopolar delivery mode when the jaws 16a, 16b are open and/or when no tissue is grasped by the jaws 16a, 16b, the second electrode portion 32 delivering monopolar energy may result in tissue not intended to receive energy delivery nevertheless receiving energy because of the relatively large surface area of the electrode 17b as compared to the first portion 30 of the electrode 17b.

In at least some embodiments the active electrode 17b can be configured to be inactive or disabled when the jaws 16a, 16b are open. In this way, energy, whether monopolar or bipolar, cannot be delivered when the jaws 16a, 16b are open. Energy delivery to unintended tissue may thus be less likely. The active electrode 17b can be configured to be inactive or disabled when the jaws 16a, 16b are open in any of a variety of ways.

In one embodiment, the sensor 18 can be configured to sense when the jaws 16a, 16b are open and to provide a signal to the processor 54 indicative of the jaws' open/closed position. The processor 54 can be configured to disable or otherwise inactivate the electrode 17b when, based on the sensed information, the jaws 16a, 16b are open. The sensor 18 can be configured to sense the open/closed position of the jaws 16a, 16b in any of a variety of ways, such as by sensing a position of the closure handle 20 relative to the stationary handle 22, sensing whether a locking feature configured to lock the closure handle 20 in position relative to the stationary handle 22 is locked or unlocked, sensing a position of a closure tube or other mechanism configured to move to cause jaw opening/closing, etc.

In another embodiment, the device 100 can include a switch configured to be engaged with the jaws 16a, 16b closed and to be disengaged with the jaws 16a, 16b open. The switch is included in the one or more electrical paths 46 configured to deliver energy in the monopolar delivery mode and energy in the bipolar delivery mode to the end effector 14. Thus, when the switch is disengaged, the energy cannot be provided to the end effector 14, effectively disabling the electrode 17b.

The electrode 17b being a singular element usable for both the monopolar delivery mode and the bipolar delivery mode may simplify and/or reduce costs of manufacturing the electrode 17b and/or the device 100. In other embodiments the electrode 17b can be two electrodes instead of one, with one electrode being configured to deliver energy in the bipolar delivery mode but not energy in the monopolar delivery mode and the other electrode being configured to deliver energy in the monopolar delivery mode but not energy in the bipolar delivery mode. Providing two electrodes may complicate and/or increase costs of manufacturing, but the two electrodes can be electrically isolated from one another to facilitate more targeted delivery of energy in the monopolar delivery mode.

Figure 11:
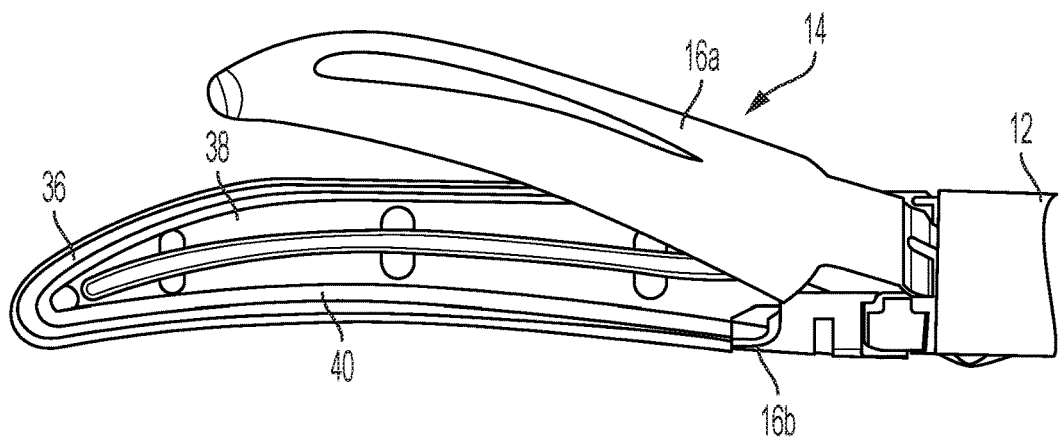
FIG. 11 is a perspective view of a distal portion of another embodiment of a surgical device with the device's jaws open.
Figure 12:
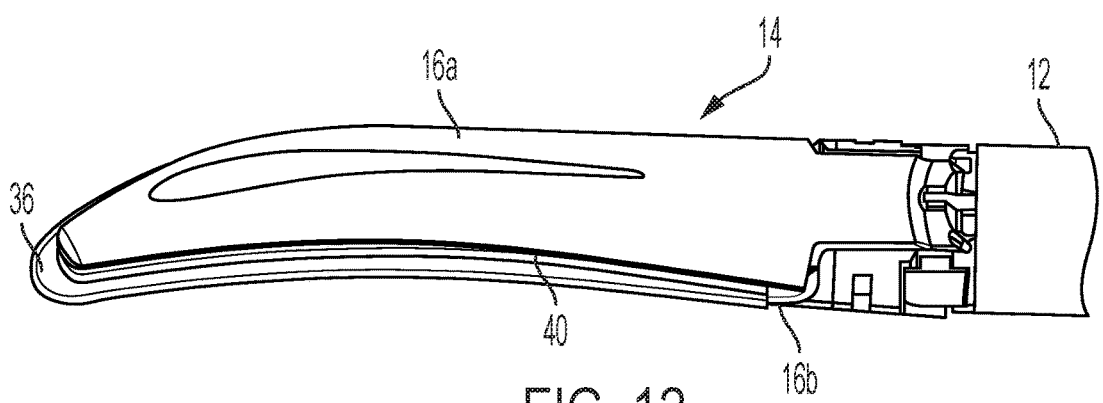
FIG. 12 is a perspective view of the distal portion of the device of FIG. 11 with the jaws closed.
Figure 13:
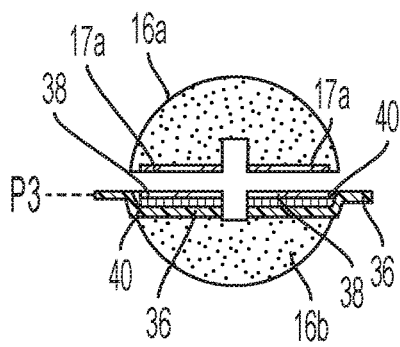
FIG. 13 is an end schematic cross-sectional view of the device of FIG. 12.

FIGS. 11-13 illustrate one embodiment of an alternate electrode configuration for the end effector 14 of FIGS. 1 and 2. The return electrode 17a is similarly present on the second jaw 16a. However, instead of having the single electrode 17b on the first jaw 16a, the electrode of the first jaw 16a includes a first portion defined by a first, monopolar electrode 36 and a second portion defined by a second, bipolar electrode 38. The end effector 14 and device 100 including the end effector 14 are otherwise configured and used similar to that discussed above regarding FIGS. 1-7 and can include any number of the alternate features described with respect to FIGS. 1-7, e.g., include a mode selector, include two sealing actuators, include a locking feature, be configured to disable energy delivery in the bipolar mode of operation (and in at least some embodiments also energy delivery in the monopolar mode of operation) when the jaws 16a, 16b are open, etc.

The first electrode 36 is in surrounding relation around the second electrode 38 similar to that discussed above regarding the first and second portions 30, 32 of the electrode 17b, but in this illustrated embodiment an insulator 40 is disposed or sandwiched between the first and second electrodes 36, 38. The insulator 40 is in surrounding relation along a perimeter of the second electrode 38, e.g., is substantially U-shaped similar to the first electrode 36, and is thus configured to electrically isolate the first and second electrodes 36, 38 from one another.

Figure 14:
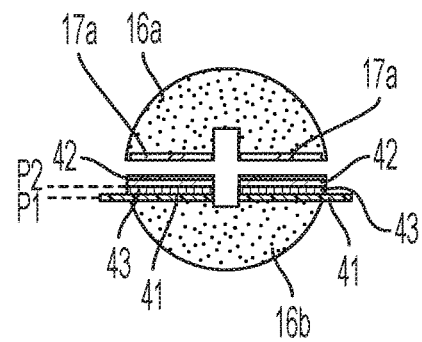
FIG. 14 is an end schematic cross-sectional view of another embodiment of a surgical device with the device's jaws closed.

FIG. 14 illustrates another embodiment an electrode configuration that includes a first portion defined by a first, monopolar electrode 41 and a second portion defined by a second, bipolar electrode 42. The embodiment of FIG. 14 is similar to the embodiment of FIGS. 11-13 except that an insulator 43 disposed or sandwiched between the first and second electrodes 41, 42 is not in surrounding relation along a perimeter of the second electrode 42. The monopolar electrode 41 thus has an inner surface that is in a plane P1 offset from a plane P2 of an inner surface of the bipolar electrode 42. In contrast, in the embodiment of FIGS. 11-13, the monopolar electrode 36 has an inner surface in the same plane P3 as an inner surface of the bipolar electrode 38. The inner surface of the monopolar electrode 36 of FIGS. 11-13 includes a step on either lateral side thereof to allow for the inner surfaces of the electrodes 36, 38 to be in the same plane P3.

Figure 15:
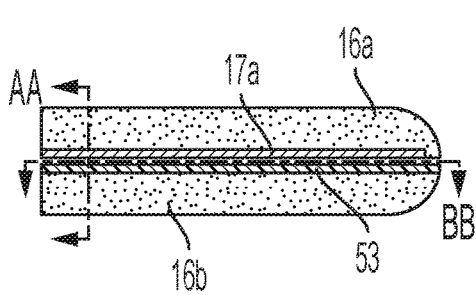
FIG. 15 is a side schematic cross-sectional view of a distal portion of yet another embodiment of a surgical device with the device's jaws closed.
Figure 16:
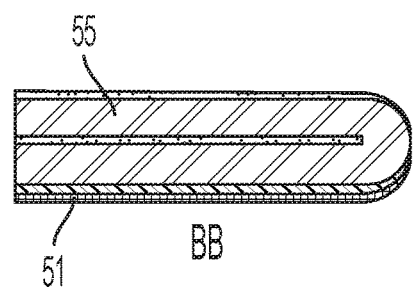
FIG. 16 is a schematic cross-sectional view of the device of FIG. 15.
Figure 17:
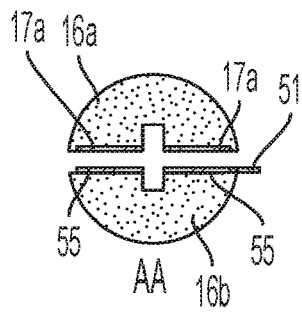
FIG. 17 is another schematic cross-sectional view of the device of FIG. 15.

The monopolar electrode in the embodiment of FIGS. 1-7 (the first portion 30 of the electrode 17*b*), the embodiment of FIGS. 8-10 (the first portion 30' of the electrode 17*b*'), the embodiment of FIGS. 11-13 (the monopolar electrode 36), and the embodiment of FIG. 14 (the monopolar electrode 41) extends along both longitudinal sides of the second electrode portion and extends laterally outward from each of the first jaw's longitudinal sides. FIGS. 15-17 illustrate one embodiment similar to the embodiment of FIGS. 8-10 except that a first, monopolar portion 51 of an active electrode 53 extends along only one longitudinal side of a second, bipolar portion 55 of the active electrode 53 and laterally outward from only one longitudinal side of the first jaw 16*b*.

Figure 18:
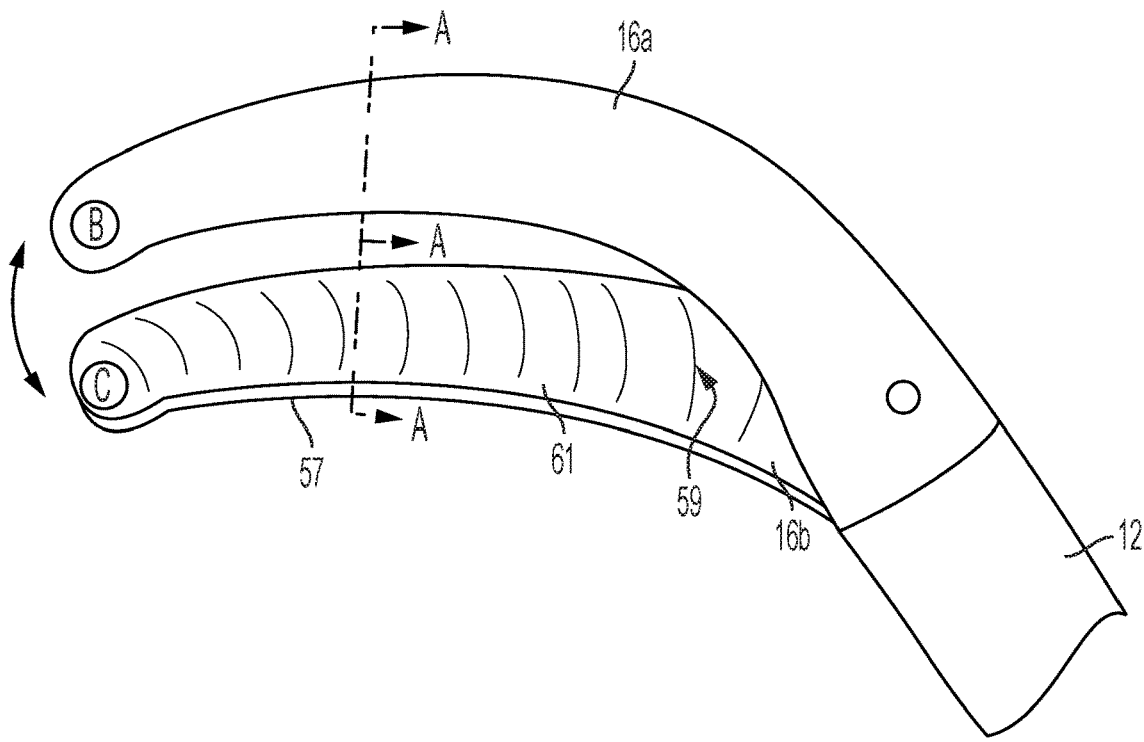
FIG. 18 is a perspective schematic view of a distal portion of still another embodiment of a surgical device with the device's jaws open.
Figure 19:
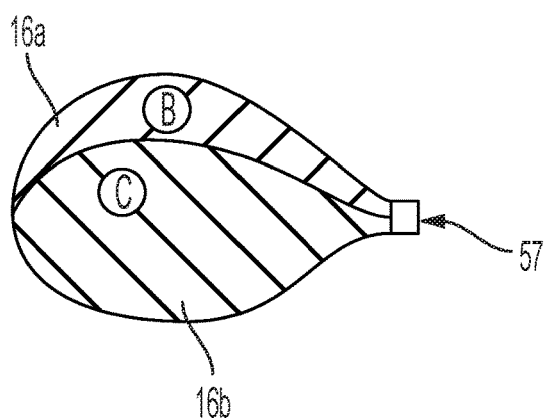
FIG. 19 is a schematic cross-sectional view of the device of FIG. 18.

FIGS. 18 and 19 illustrate another embodiment similar to the embodiment of FIGS. 15-17 in which a first, monopolar portion 57 of an active electrode 59 extends along only one longitudinal side of a second, bipolar portion 61 of the active electrode 59 and laterally outward from only one longitudinal side of the first jaw 16*b*. However, in the embodiment of FIGS. 18 and 19 the monopolar portion 57 also extends around the distal tip of the bipolar portion 61. Additionally, as best shown in FIG. 19 tissue-contacting surfaces of each of the jaws 16*a*, 16*b*, e.g., tissue-contacting surfaces of the return electrode 17*a* and the bipolar portion 61, are curved in this illustrated embodiment instead being substantially planar as in the embodiments of FIGS. 1-17. Any of the embodiments of jaws described herein can have curved or substantially planar tissue-contacting surfaces, with jaws of the same surgical device either each being curved or each being substantially planar.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An electrosurgical device, comprising:
   a housing;
   an elongate shaft extending from the housing;
   an end effector coupled to a distal end of the elongate shaft, the end effector including first and second jaws, at least one of the first and second jaws being pivotable relative to the other to move the end effector between an open position and a closed position; and
   first and second electrode portions on the first jaw, the first electrode portion being in surrounding relation along a perimeter of the second electrode portion such that the first electrode portion is positioned laterally outward of the second electrode portion, the first electrode portion being configured to be exposed along an edge of the first jaw with the end effector in the closed position and with the end effector in the open position;
   wherein in a bipolar mode of operation the second electrode portion is configured to deliver energy to tissue engaged by the end effector, and the first electrode portion is disabled from delivering energy to tissue engaged by the end effector;
   wherein in a monopolar mode of operation the first electrode portion is configured to deliver energy to tissue; and
   wherein a single electrode includes the first and second electrode portions with the first electrode portion being U-shaped and in surrounding relation along longitudinal sides and around a distal tip of the second electrode portion, which is in direct contact with the first electrode portion along the longitudinal sides and around the distal tip.

2. The device of claim 1, wherein in the monopolar mode of operation the second electrode portion is one of disabled from delivering energy to tissue and enabled to deliver energy to tissue.

3. The device of claim 1, wherein the second jaw has a width that is less than a combined width of the first and second electrode portions.

4. The device of claim 1, further comprising a return electrode on the second jaw, the return electrode being configured for energy return in the bipolar mode of operation.

5. The device of claim 1, further comprising a sensor configured to sense when the end effector is in the closed position; and
   an actuator configured to be actuated to cause energy delivery in the bipolar mode of operation only with the end effector in the closed position as sensed by the sensor.

6. The device of claim 5, wherein the monopolar mode of operation is only possible with the end effector in the open position.

7. The device of claim 6, further comprising a second actuator configured to be actuated to cause energy delivery in the monopolar mode of operation.

8. The device of claim 1, wherein the monopolar mode of operation is possible with the end effector in the open position and in the closed position.

9. The device of claim 1, wherein the first electrode portion, but not the second electrode portion, has a coating thereon.

10. An electrosurgical device, comprising:
    a housing;
    an elongate shaft extending from the housing; and
    an end effector coupled to a distal end of the elongate shaft, the end effector including first and second jaws, at least one of the first and second jaws being pivotable relative to the other to move the end effector between an open position and a closed position;
    wherein an electrode on the first jaw extends laterally outward from an outer edge of the first jaw such that with the end effector in the closed position the electrode is exposed, thereby allowing the electrode to contact tissue with the end effector in the closed position and without any tissue being engaged between the first and second jaws;
    the electrode is configured to deliver energy to tissue with the end effector in the open position and with the end effector in the closed position;
    the electrode is a single electrode; and
    a U-shaped portion of the electrode extends laterally outward from the outer edge of the first jaw and is in surrounding relation along a perimeter of a second portion of the electrode such that the U-shaped portion of the electrode is positioned laterally outward of the second portion of the electrode.

11. The device of claim 10, wherein
    in a bipolar mode of operation the second portion of the electrode is configured to deliver energy to tissue and the U-shaped portion of the electrode is disabled from delivering energy to tissue; and in a monopolar mode of operation the U-shaped portion of the electrode is configured to deliver energy to tissue.

12. The device of claim 11, further comprising a sensor configured to sense when the end effector is in the closed position; and
   an actuator configured to be actuated to cause energy delivery in the bipolar mode of operation only with the end effector in the closed position as sensed by the sensor.

13. The device of claim 11, wherein the monopolar mode of operation is possible with the end effector in the open position and in the closed position.

14. A surgical method, comprising:
   positioning an end effector of a surgical device in contact with tissue, the end effector being coupled to a distal end of an elongate shaft of the surgical device, the end effector including first and second jaws, first and second electrode portions being on the first jaw with the first electrode portion being U-shaped an in surrounding relation along a perimeter of the second electrode portion such that the first electrode portion is positioned laterally outward of the second electrode portion;
   activating the surgical device in a bipolar mode of operation such that the second electrode portion, but not the first electrode portion, delivers energy to the tissue; and
   activating the surgical device in a monopolar mode of operation such that the first electrode portion delivers energy to the tissue.

15. The method of claim 14, wherein in the monopolar mode of operation the second electrode portion cannot deliver energy to the tissue.

16. The method of claim 14, further comprising sensing with a sensor when the end effector is in a closed position;
   wherein activating the surgical device in the bipolar mode of operation is only possible with the end effector in the closed position as sensed by the sensor; and
   activating the surgical device in the monopolar mode of operation is only possible with the end effector in an open position.

17. The method of claim 14, wherein activating the surgical device in the monopolar mode of operation is possible with the end effector in an open position and in a closed position.

* * * * *